United States Patent
Nafisi-Movaghar et al.

[11] Patent Number: 5,912,363
[45] Date of Patent: Jun. 15, 1999

[54] METHOD FOR EXTRACTION OF PROANTHOCYANIDINS FROM PLANT MATERIAL

[75] Inventors: Karim Nafisi-Movaghar; Thomas T. Svanoe; William A. Seroy, all of Concord, Calif.

[73] Assignee: Interhealth Nutraceuticals, Concord, Calif.

[21] Appl. No.: 08/919,805

[22] Filed: Aug. 29, 1997

[51] Int. Cl.$^6$ .......................... C07D 311/62; C07D 315/00
[52] U.S. Cl. ............................................ 549/399; 549/415
[58] Field of Search ...................................... 549/399, 415

[56] References Cited

U.S. PATENT DOCUMENTS

5,484,594  1/1996  Frangi et al. .

*Primary Examiner*—Johann Richter
*Assistant Examiner*—Taofiq A. Solola
*Attorney, Agent, or Firm*—James C. Weseman, Esq.

[57] ABSTRACT

A method for the extraction of proanthocyanidins from plant material is disclosed. The method involves heating an aqueous mixture of solid plant material, optionally under increased pressure and reduced oxygen; various separation, filtration and adsorption steps, and the elution of adsorbed proanthocyanidins with polar solvent. Optionally, the polar solvent can be reconstituted and recycled into the elution phase of the method, resulting in decreased solvent consumption.

9 Claims, 5 Drawing Sheets

METHOD FOR EXTRACTION OF PROANTHOCYANIDINS FROM PLANT MATERIAL

TECHNICAL FIELD

The present invention relates to the extraction of flavonoid compounds from plant material, and, more particularly, to the extraction of proanthocyanidins.

BACKGROUND OF THE INVENTION

Flavonoid compounds are present in all aerial parts of plants, with high concentrations found in the skin, bark, and seeds. Such compounds are also found in numerous beverages of botanical origin, such as tea, cocoa, and wine. The flavonoids are a member of a larger family of compounds called polyphenols. That is, these compounds contain more than one phenol group (OH) on the respective benzene ring. The physical and chemical properties, nomenclature, analysis and biological activities of polyphenols and particularly flavonoids have been studied for many years.

Proanthocyanidins are a particular class of colorless flavonoid compounds with a general structure as follows:

Proanthocyanidin Dimer Form (Catechin Dimer)

Proanthocyanidins yield anthocyanin upon hydrolysis with inorganic acids, and anthocyanins are responsible for the reddish color of grapes, flowers and other plant materials.

Bate-Smith and Bate-Smith and Lerner (1954) systematically investigated a broad variety of flavonoid compounds. The acid hydrolysis of proanthocyanidins, in addition to anthocyanidins, yields catechin. Catechin is the building unit of dimers, trimers and oligomers. Catechin, a flavonoid, exists in two isomeric forms as follows:

(-)-Epicatechin (cis form)

(+)-d-Catechin

The proanthocyanidin which produces catechin and anthocyanidin is called proanthocyanidinocatechin for this class of natural products.

Aside from the different components of the dimers and oligomers, absolute configurations, i.e., optically active molecules, also contribute to a wide range of proanthocyanidins. For example, for the first noted structure, 32 optically-active forms are possible. Oligomeric proanthocyanidins (OPCs) occur in nature in a wide range of plants, including grape seeds.

The antioxidant properties of phenolic compounds, such as vitamin E (a non-flavonoid monophenolic compound) and especially polyphenols, such as proanthocyanidins, are well-documented. These compounds are free radical scavengers in biological systems. The oxygen molecule ($O_2$) is involved in the respiratory process under normal conditions. Under certain conditions, however, it can be transformed into superoxide anion ($O_2$), hydroxyl radical (OH), singlet oxygen ($O_2\Delta$ g), and/or hydrogen peroxide ($H_2O_2$). The superoxide anion, the hydroxyl radical, and specifically, singlet oxygen (free radicals), are responsible for anemia and aging (leathery-looking skin), and stress (prostate problems, etc.). Proanthocyanidins are also known to protect cells from lipid peroxidation, resulting in the protection of target organs' membranes. An example is the protection of low density lipoproteins (LDL; so-called bad cholesterol) from oxidation. The oxidation of LDL is a contributing factor to atherosclerosis and cardiovascular disease. A variety of proanthocyanidins have been effective in preventing the growth of breast cancer cells. Proanthocyanidins are very potent free radical scavengers and metal chelators. They reduce free radicals, a by-product of metabolism and block their propagation. The complexity of the proanthocyanidins results from their biological diversity.

In order to capture many, but nonetheless a selective group, of these flavanoid compounds, well-defined and precise processing and separation techniques are needed. There have been previous attempts to separate proanthocyanidins (Frangi et al., U.S. Pat. No. 5,484,594) from plant material. This process involved the preparation of an extract, enriched in procyanidol oligomers, using organic solvents. The organic solvents used include acetone and methanol (as primary solvents), ethyl acetate, methylene chloride and dichloroethane. This organic extraction process has a number of drawbacks:

First, the procedure is not very efficient since the extraction is performed at room temperature, and the organic solvents exclude many of useful proanthocyanidins during the extraction procedure.

Next, the procedure requires the use of consecutive ultrafiltration and storage of the product for 24 hours at a cold temperature; as the procedure involves many steps, it is cumbersome. Furthermore, the solvents employed in the procedure are problematic: The procedure uses a chlorinated hydrocarbon which is a known carcinogen; it is not practical to totally eliminate acetone, methanol, and ethyl acetate in the presence of water without forming an azeotropic mixture; and, by using very reactive acetone and chlorinated hydrocarbons (even though they are eliminated from the final product), there exists the possibility of a reaction of the proanthocyanidins with these solvents, and therefore, an alteration in the nature of the extracted proanthocyanidins.

In addition, the use of these chlorinated hydrocarbons and other solvents pose an environmental hazard. Disposal is difficult and cumbersome, and the vapors are hazardous to workers.

Disclosure of the Invention

The present invention provides a method for the extraction of proanthocyanidins from plant material. The present method can use any source of proanthocyanidins (hereafter interchangeably termed 'OPCs'), most typically from botanically-derived plant material such as seeds, skins, vegetables, nuts, tree barks, and any other OPC-rich plant material. The raw material may be used either as is (wet) or may be presorted by drying, separating and removing the components low in OPCs. One embodiment of the present invention utilizes grape (Vitis vinifera) seed, from various varieties, such as Merlot, Cabernet, and the like.

In one aspect, the method comprises the steps of providing an aqueous mixture of solid plant material containing proanthocyanidins. The mixture is heated, optionally under increased pressure and/or reduced oxygen, to produce an aqueous solution containing extracted proanthocyanidins, and the aqueous solution is separated from the residual solid material. The aqueous solution is then filtered to remove larger molecular weight polymers and particulates, to produce a permeate containing extracted proanthocyanidins. The extracted proanthocyanidins are separated from the permeate liquid by contacting the permeate with an adsorbent material which is capable of releasably retaining the extracted proanthocyanidins, and the proanthocyanidins retained on the adsorbent material are eluted with a polar solvent. Finally, the eluted proanthocyanidins are concentrated to produce a concentrated proanthocyanidin extract. Desirably, the concentrated proanthocyanidin extract is dried, optionally under reduced pressure, to remove residual liquid.

In another aspect of the invention, the polar solvent can be reconstituted and recycled into the desorption phase of the method, resulting in low solvent consumption.

DESCRIPTION OF THE DRAWINGS

FIG. 2 is a schematic view of a flow chart for one embodiment of the method of the present invention performed at an industrial scale;

DETAILED DESCRIPTION OF THE INVENTION

The present invention provides a method for the extraction of proanthocyanidins from plant material. In one aspect, the method comprises the steps of providing an aqueous mixture of solid plant material containing proanthocyanidins. The mixture is heated, optionally under increased pressure and/or reduced oxygen, to produce an aqueous solution containing extracted proanthocyanidins, and the aqueous solution is separated from the residual solid material. The aqueous solution is then filtered to remove larger molecular weight polymers and particulates, to produce a permeate containing extracted proanthocyanidins. The extracted proanthocyanidins are separated from the permeate liquid by contacting the permeate with an adsorbent material which is capable of releasably retaining the extracted proanthocyanidins, and the proanthocyanidins retained on said absorbent material are eluted with a polar solvent. Finally, the eluted proanthocyanidins are concentrated to produce a concentrated proanthocyanidin extract. Desirably, the concentrated proanthocyanidin extract is dried, optionally under reduced pressure, to remove residual liquid.

In another aspect of the invention, the polar solvent can be reconstituted and recycled into the desorption phase of the method, resulting in low solvent consumption.

Figure 1:
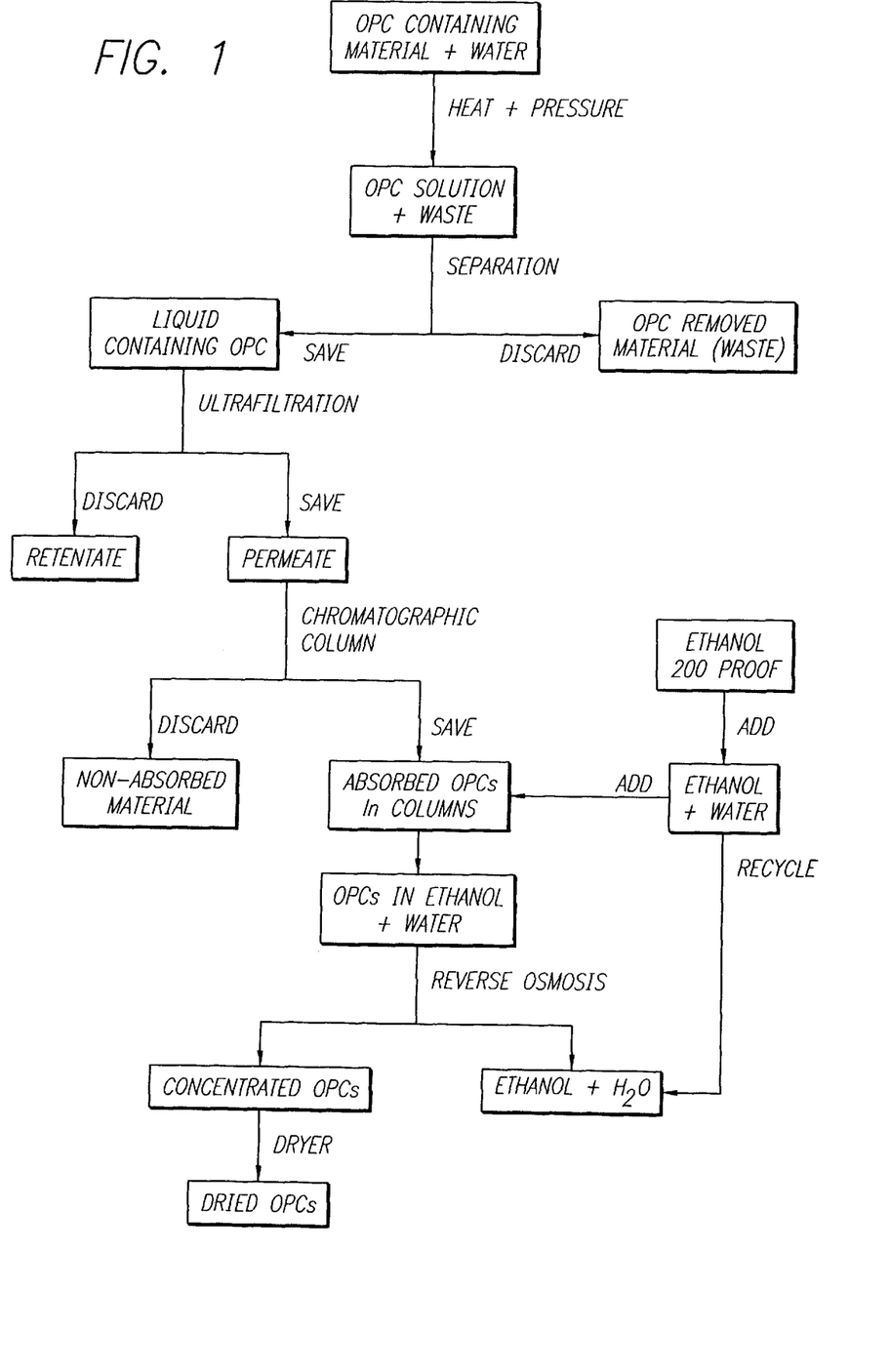
FIG. 1 is a schematic view of a flow chart for one embodiment of the method of the present invention.

The present invention is capable of producing a very potent proanthocyanidin extract with an excellent free radical scavenging ability. The extract has been shown to be more effective than vitamin C and vitamin E in free radical scavenging ability, as demonstrated by in vitro experiments, and more effective than vitamin C, vitamin E and beta-carotene in inhibiting free radical-induced cellular damage, as demonstrated by in vivo experiments. Schematic views of selected embodiments of the present method are shown in FIGS. 1 and 2.

The present method can use any source of proanthocyanidins (hereafter interchangeably termed 'OPCs'), most typically from botanically-derived plant material such as seeds, skins, vegetables, nuts, tree barks, and any other OPC-rich plant material. The raw material may be used either as is (wet) or may be presorted by drying, separating and removing the components low in OPCs. One embodiment of the invention utilizes grape (Vitis vinefera) seed, from various varieties, such as Merlot, Cabernet, and the like.

The present method comprises a number of separate phases, which, taken together, produce the beneficial results. However, it will readily be appreciated that the division of the method into separate phases is an artificial construct, primarily to aid in the clarity of presenting the invention, and that various aspects of any particular phase may be performed out of the described order, or combined with aspects ascribed to other phases, while still obtaining the benefits of the invention. The representative phases of the invention can be described generally as follows:

Extraction Phase

During this initial phase, an aqueous mixture of solid plant material containing proanthocyanidins is formed, and the mixture is heated, optionally under increased pressure and reduced oxygen, to produce an aqueous solution containing the extracted proanthocyanidins. Thereafter, the aqueous solution is separated from the residual solid plant material (debris).

For example, on an industrial scale about 400 pounds of solid plant material and 300 gallons of water, preferably water at about 1:6 to 1:10 solid to water ratio, are mixed in a heating pressure vessel, desirably equipped with a pressure gauge and a thermometer. When using grape seed as the solid plant material, wet grape pumice can be obtained from wineries, and optionally air dried and cleaned by separating the seeds from the skin or by separating the skin from the seed and then drying the seeds. Deionized water is preferred in forming the mixture because OPCs are chelators and any metal ion, especially ions of transition elements, may bind to the OPCs and cause decreased OPC yield. The ratio of seed to water may vary from 5:1 to 1:600. The mixture will be heated to a temperature between 60–350° F., optionally at atmospheric to 80 psi pressure, preferably 180–250° F. and 2–60 psi pressure, and desirably 180–250° F. and 2–40 psi pressure. The heating time will vary, depending in part on the temperature and pressure selected, generally ranging from 5 minutes to 5 hours, preferably between 10 to 40 minutes.

Optionally, it may be desirable to perform this phase of the method under reduced oxygen as well. This reduced oxygen condition can be established by evacuating the chamber, by flushing with other gases, desirably atmospheric gases such as nitrogen, or by increasing the pressure in the extraction chamber with oxygen-free or reduced-oxygen gases.

After heating, the separation of the liquid mixture from the debris is accomplished, for example, by pumping the mixture over a parabolic screen and the separated solids are discarded or reheated with water again for further OPC separation.

Filtration Phase

During this phase, the aqueous solution obtained from the extraction is filtered, desirably through a membrane, to remove larger molecular weight polymers and particulates, and to produce a clarified permeate containing the extracted proanthocyanidins. Preferably, the filtration is performed by ultrafiltration, e.g., through a polymeric membrane.

Again on an industrial scale, the separated aqueous solution is pumped into a 2,000 gallon tank designated as the ultrafiltration (UF) feed tank. To clarify the liquid in the UF feed tank, clarifying agents, such as polyvinylpyrrolidone (PVP) or bentonite can be used if desired. These clarifying agents are known materials and have been used extensively for many years to clarify fruit juices, wine, and beer, without cause for concern. As a representative example, Bentonite will be added at a rate of about 0.5–10% of the weight of the extracted liquid, preferably, about 2.5% of the weight. The Bentonite may then be decanted before feeding the liquid to the UF unit, although it is possible to feed the UF unit without decanting the mixture. The clarifying agent can also be removed by filtration, or by any conventional process, such as by frame and plate, or by a pre-coated vacuum filter (DE filtration) or by microfilteration. It should however be appreciated that the addition of any clarifying agents is entirely optional.

Ultrafiltration can be performed with or without cooling the extracted liquid. The proper selection of the filtration membrane and the operating parameters allows OPC molecules to permeate the filter, and high molecular weight tannin-like materials, including clarifying agents, will remain behind.

Figure 3:
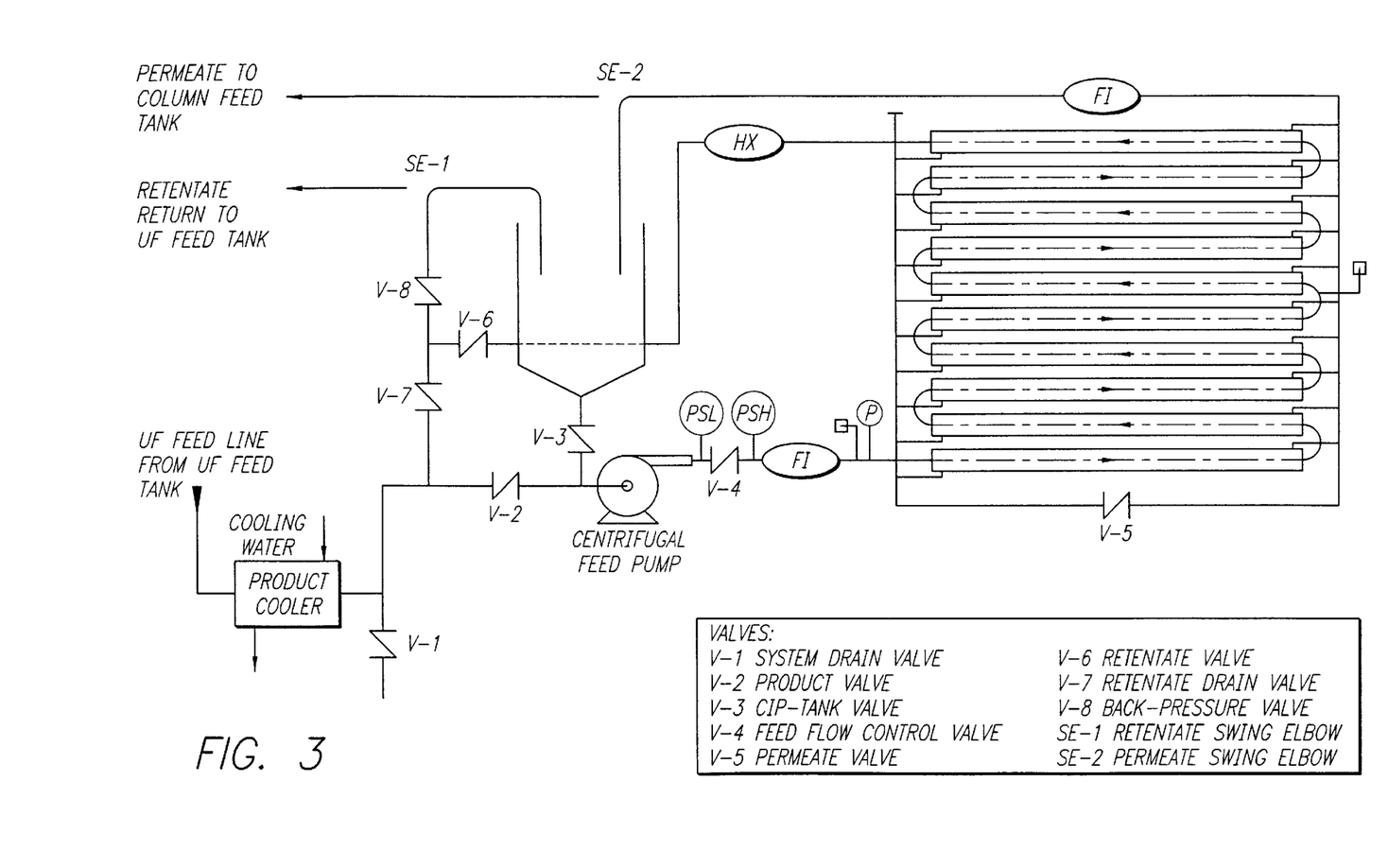
FIG. 3 is a schematic view of a flow chart for one embodiment of the filtration phase of the method of the present invention.

During filtration, for every 100 gallons of extracted liquid, approximately 60 gallons of deionized water, about 37%, is added (diafiltration). The addition of deionized water is desirable because it contains no silicon, nor transition elements, such as iron (Fe), copper (Cu) and nickel (Ni) ions. The presence of these chemicals can cause fouling of the UF membrane. A representative schematic view of the ultrafiltration phase is shown in FIG. 3.

The process parameters for this phase of the method are generally as follows: The clarified extract can be subjected to the UF unit desirably at about 20–200 gallons per minute (gpm), preferably at approximately 8 gpm. The operating pressure will desirably range from about 60–200 psi, and preferably approximately 100 psi. The operating temperature will desirably range from about 40–180° F., and preferably approximately 125° F. The molecular weight cut off for the membrane is desirably about 5,000–500,000 mw and preferably approximately 200,000 mw. A PCI membrane, FP-200, provides a desirable filter for this phase of the method.

Adsorption Phase

This phase of the method involves separating the extracted proanthocyanidins from the permeate solution by contacting the permeate with an adsorbent material which is capable of releasably retaining the extracted proanthocyanidins, and eluting the proanthocyanidins retained on the absorbent material with a polar solvent. Typically, OPCs are adsorbed onto a carefully selected adsorbent resin packed in a column. The resins used are typically generally non-ionic in nature. However, although non-ionic, the resins used will have a very weak anionic (weak base) character.

After preparation and careful size classification of the resins in the column (in order to facilitate packing and improve flow characteristics), the permeate generated by ultrafiltration is passed through the resin in the column (termed "charging the column"). The OPCs are selectively adsorbed by the resin, and will be loosely bound generally only by Van der Waal's forces.

The process parameters of this phase of the method play a major role in isolation and purification of the desirable OPCs: Again on an industrial scale, the column used for the method can be approximately 18" in diameter and 156" in height. It is generally packed by approximately 7 ft$^3$ (one bed volume (BV)) of adsorbent resin, expandable up to approximately 9 ft$^3$ resin.

The resin employed is desirably XUS-43520 00, a hydrophobic, microporous divinylbenzene copolymer, manufactured by a proprietary process by Dow Chemical, and used in accordance with the instructions provided by the manufacturer and regulations established by the United States Food and Drug Administration. The resins are generally supplied in the form of spherical beads. The resins used will desirably have the following physical properties:

Surface area in the range of 100–300 m²/g;
Pore volume of 1–6 cc/g;
Pore size with an average radius in the range of 5–200 Å;
Particle size in the range of 5–300 standard mesh.

Any similar resin, and optionally hydrophilic resins, can be used in the present method. The permeate feed rate is desirably about 0.5–20 bed volumes (BV) per hour, and preferably approximately 1–4 BV. The permeate temperature range is desirably about 40–210° F., and preferable about 80–150° F. The permeate is generally passed through the resin column without requiring any pH alteration (the pH of the permeate is generally in the range of 3.5–4.5). The adsorbent resin will saturate after passing approximately 20–50 BV of the UF permeate under normal operating conditions, i.e., at 1–4 BV flow rate and 80–150° F.

OPCs adsorbed on the column (loosely bound to the resin) can be eluted (desorbed) by any polar solvent or mixture of solvents, including, e.g., hot water in the range of approximately 200–240° F. However, the preferred solvent for eluting the adsorbed OPCs is food grade ethanol, from approximately 5–100% concentration, or a mixture of any other polar solvents with substantially equivalent polarity. Aliquots of the eluent can be monitored during elution to determine when substantially all of the adsorbed OPCs have been eluted. OPCs collected in this manner from the column are then transferred into a tank for concentration.

In another aspect of the invention, the polar solvent can be reconstituted and recycled into the desorption phase of the method, resulting in low solvent consumption on an industrial scale. For example, as described below, the OPC-depleted ethanol/water solution produced during the concentration phase of the method can be reconstituted and recycled in this phase of the method.

Resins used in the present method not only bind OPCs, which are removed by the polar solvents such as e.g. a water-alcohol mixture, they also bind any other organic/inorganic compounds. These compounds are generally not removed by eluting the resins with polar solvents. Accumulation of the unwanted organic and inorganic compounds by prolonged usage of the resin results in saturation of the adsorbent resin and reduces the resin capacity.

It has been discovered that it is desirable to remove these unwanted compounds and regenerate the resins periodically. The regeneration will be done generally after passing every 500–50,000 BV of UF permeate through the resin bed. The regeneration of the resins involves:

a. Washing the resins with deionized water after eluting the OPCs;

b. Treating the resins with about 1–20 BV of a 0.01–10% solution of a caustic agent, such as sodium hydroxide, at a rate of about 0.5-10 BV/hr, and a temperature range of from 50–250° F.;

c. After removing the caustic solution, the resins are washed with water to a pH value in the range of approximately 7–12;

d. After washing with water, the resin is then washed with any acid, preferably an organic acid, e.g. citric or lactic acid, at a 0.01–10% concentration and a temperature in the range of from 40–250° F., preferably at approximately 140° F. Inorganic acids, such as sulfuric acid, hydrochloric acid and phosphoric acids, will also prove useful.

e. Excess acid is removed and the residual acid is washed out of the resin to a pH range of 2–7, preferably 4–5.

The water temperature may range from 40–250° F., preferably from 100–150° F.;

f. The resin is then backwashed, as done conventionally, to expand to at least 50% of its original volume.

Concentration Phase

During this phase of the method, the eluted OPCs are concentrated, preferably by Reverse Osmosis (RO) to produce a concentrated proanthocyanidin extract. Optionally, the permeate liquid of the reverse osmosis can be reconstituted to minimize consumption of the polar solvent.

Figure 4:
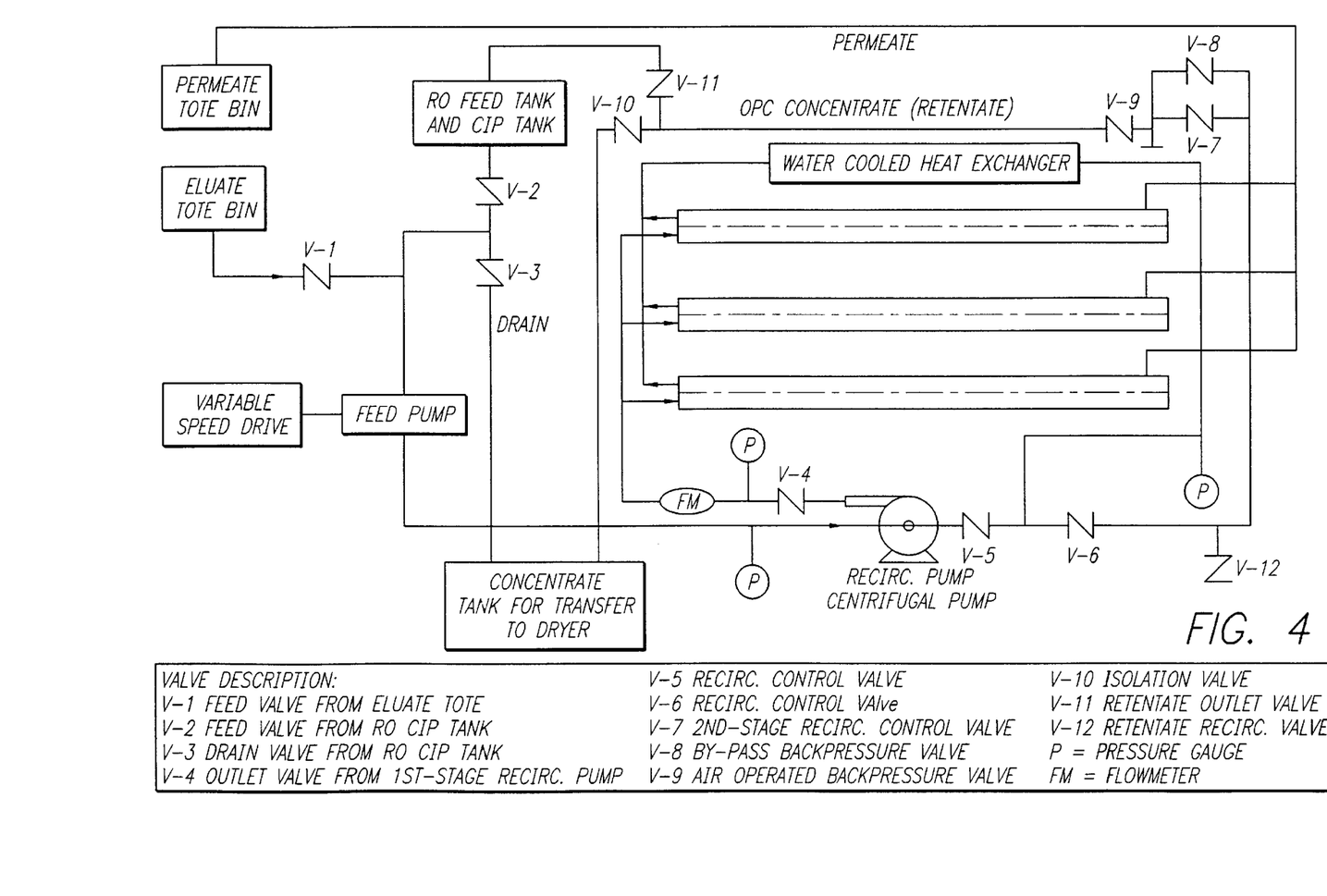
FIG. 4 is a schematic view of a flow chart for one embodiment of the reverse osmosis concentration phase of the method of the present invention.

The concentration of the OPCs collected in the adsorption phase of the method is comparatively low. Preconcentration of the OPCs is one of the steps taken to make this method more economically feasible (FIG. 4). The desirability of this step is threefold: First, it accelerates the drying time which in turn prevents OPC fragmentation resulting from prolonged drying times. Second, by preconcentration, a mixture of solvents recovered (permeate) can be recycled, which results in removing OPCs from the adsorbent material. In addition to the economic advantage, it is also an environmentally sound method. Third is the selection of a desirable RO membrane and operating conditions to produce selective groups of OPCs.

The steps for the concentration OPCs are illustrated in FIG. 4. The operation conditions for the RO include:

–The OPC solution is desirably fed at 5–150 gallons per minute (gpm), preferably at approximately 20 gpm;

–The operating pressure desirably ranges from 100–1000 psi;

–The feed temperature desirably ranges from 40–180° F., preferably approximately 120° F.

–The RO membrane employed will desirably have permeation from 99.5% salt (sodium chloride) rejection (tightest) to 5000 MW cut off (loosest). The preferred exclusion cut off point of the membrane is 1000–2000 MW;

–The RO membrane utilized will desirably have 50–5000 MW cut off;

–The permeate from RO is a mixture of water/alcohol solution, generally approximately 15–20 percent alcohol. The retentate from RO is generally approximately 10–40% OPC solids. The RO permeate is desirably adjusted to 15–50 percent alcohol, preferably to 20 percent, using 100 percent grain alcohol (ethanol), and used again as an eluant to desorb OPCs adsorbed on the resins in the column.

Drying Phase

During this optional phase of the method, the concentrated OPC extract can be dried, optionally under reduced pressure, to remove residual water and solvent. Typically, this drying phase is accelerated by heating.

In this phase, RO retentate is transferred into any conventional dryer, such as a drum dryer, cabinet dryer, spray dryer, freeze dryer, etc., preferably a vacuum-assisted dryer, to remove the water and solvent. The OPC-enriched powder obtained from the dryer is then desirably cooled, ground and packaged in an air- and moisture-tight container.

Drying can be advantageously achieved in a range from approximately 50° F.–230° F. at atmospheric pressure, or optionally from 40° F.–220° F. at reduced pressures from 1–30" Hg. The preferred conditions for drying are at approximately 25" Hg and 165° F.

The following examples serve to illustrate certain preferred embodiments and aspects of the present invention and are not to be construed as limiting the scope thereof.

Experimental

In the experimental disclosure which follows, all weights are given in grams (g), milligrams (mg), micrograms (μg), nanograms (ng), or picograms (pg), all amounts are given in moles (mol), millimoles (mmol), micromoles (μmol), nanomoles (nmol), picomoles (pmol), or femtomoles (fmol), all concentrations are given as percent by volume (%), proportion by volume (v:v), molar (M), millimolar (mM), micromolar (μM), nanomolar (nM), picomolar (pM), femtomolar (fM), or normal (N), all volumes are given in liters (L), milliliters (mL), or microliters (μL), and linear measurements are given in millimeters (mm), or nanometers (nm) unless otherwise indicated.

The following examples demonstrate the practice of the present invention in obtaining a proanthocyanidin-enriched extract from plant material.

EXAMPLE 1

In order to form an aqueous mixture, 400 pounds of dry, cleaned *Vitis vinifera* grape seed (or any other species of the Genus Vitis, or any crossed hybrids) are conveyed into a pressure vessel containing 300 gallons of deionized water. The mixer in the vessel is turned on and 25 pounds of bentonite is added into the vessel. The vessel is closed and the contents are heated at 240° F. for 2 hours. The mixture is then cooled and pumped over a parabolic screen to separate the seeds and some of the bentonite from the liquid extract.

The extract is then filtered by a PCI ultrafiltration (UF) unit equipped with a FP-200 membrane at 80 gpm and 125° F. To facilitate filtration, additional water at approximately 37% of the extract volume is added (diafiltration) during the procedure.

The permeate (about 1600 gallons) is then pumped into a separation column containing the adsorbent resin XUS-43520.00, a divinylbenzene copolymer manufactured by Dow Chemical, at 3 BV flow rate. The resin is then washed with 20% ethanol at 120° F. One thousand gallons of OPC in water-alcohol (solution) is thus generated.

The eluted OPCs are then concentrated by reverse osmosis using an ES404 membrane. Twenty gallons of concentrated OPC extract is transferred into a vacuum dryer and dried at 175° F. and 29–30" Hg for six hours. Thirty-two pounds of dry OPC extract is obtained and packaged for further grinding.

EXAMPLE 2

An OPC extract according to the invention is prepared in the same manner as described in Example 1, except that the permeate from the reverse osmosis operation is further heated, fortified with 15 gallons of absolute ethanol and used to elute the OPCs from the adsorbent resins in the resin column.

EXAMPLE 3

An OPC extract according to the invention is prepared in the same manner as described in Example 1, except that grape pumice (a mixture of seed and skin) is substituted for the grape seed as the solid plant material.

EXAMPLE 4

An OPC extract according to the invention is prepared in the same manner as described in Example 1, except that almond or walnut hulls are substituted for the grape seed as the solid plant material.

EXAMPLE 5

An OPC extract according to the invention is prepared in the same manner as described in Example 1, except that pine bark is substituted for the grape seed as the solid plant material.

All patents and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

REFERENCES

U.S. Pat Documents:
*Process for Preparing Grapeseed Extract Enriched in Procyanidol Oligomers.* U.S. Pat. No. 5,484,594.
*Plant Extract with a Proanthocyanidins Content as Therapeutic Agent Having Radical Scavenger Effect and Use Thereof.* U.S. Pat. No. 4,698,360.
Other Publications:
Markakis, Pericles (1982) *Anthocyanins as Food Colors* (Markakis, P., ed.), pp. 163–180. Academic Press.
Takuo Okuda et al "Pharmacologically Active Tannins Isolated from Medicinal Plants." *Plant Plyphenols,* edited by R. W. Hemmingway and P. E. Laks, Plenum Press, New York, 1992.
Bate-Smith, E. C., and Lerner, N. H. (1954) Biochem. J. 58, 126.
Bate-Smith, E. C. (1954) BioChem. J. 58, 122.
Lea, G. H. et al *The Phenolics of Ciders: Effect of Processing Conditions.* J. Sci. Fd. Agric. 1978, 29, 484–492.
Torel, J. et al. *Antioxidant Activity of Flavonoids and Reactivity with Peroxy Radicals.* Phytochemistry, vol. 25, No. 2., pp. 383–385, 1986.

We claim:

1. A method for the extraction of proanthocyanidins from plant material comprising:
    (a) providing an aqueous mixture of solid plant material containing proanthocyanidins;
    (b) heating the mixture to produce an aqueous solution containing extracted proanthocyanidins;
    (c) separating said aqueous solution from the residual solid material;
    (d) filtrating said aqueous solution to remove larger molecular weight polymers and particulates to produce a permeate containing extracted proanthocyanidins;
    (e) separating the extracted proanthocyanidins from the permeate solution by contacting the permeate with an adsorbent material which is capable of releasably retaining the extracted proanthocyanidins;
    (f) eluting the proanthocyanidins retained on said absorbent material with a polar solvent; and
    (g) concentrating the eluted proanthocyanidins to produce a concentrated proanthocyanidin extract and a second permeate liquid.

2. The method of claim 1, further comprising adding sufficient polar solvent to the second permeate liquid of step (g) so as to approximately reconstitute the original polar solvent concentration; and utilizing the reconstituted second permeate as at least a portion of the polar solvent of step (f).

3. The method of claim 1 wherein the aqueous mixture is formed in a ratio of from approximately 1:6 to 1:10 (w/w; water to solid).

4. The method of claim 1 wherein the aqueous mixture of step (b) is subject to an increased pressure of from approximately 2 to 40 psi, and a temperature of from approximately 180 to 250° F.

5. The method of claim 1 wherein said aqueous solution is filtered through a membrane with an exclusion value of from approximately 2,000 to 200,000 mw.

6. The method of claim 1 wherein said permeate is contacted with an adsorbent material comprising a hydrophobic or hydrophilic divinylbenzene copolymer resin.

7. The method of claim 1 wherein said polar solvent comprises ethanol.

8. The method of claim 7 wherein said polar solvent comprises approximately 5–100% ethanol in aqueous solution.

9. The method of claim 1 wherein said eluted proanthocyanidins are concentrated by Reverse Osmosis through a membrane with an exclusion value of from approximately 1,000 to 2,000 mw.

* * * * *